United States Patent
Laaksonen et al.

(10) Patent No.: US 10,850,120 B2
(45) Date of Patent: Dec. 1, 2020

(54) SELECTING A DOSE PREDICTION MODEL BASED ON CLINICAL GOALS

(71) Applicant: Varian Medical Systems International AG, Cham (CH)

(72) Inventors: Hannu Laaksonen, Espoo (FI); Esa Kuusela, Espoo (FI); Janne Nord, Espoo (FI); Joakim Pyyry, Helsinki (FI); Perttu Niemela, Espoo (FI)

(73) Assignee: Varian Medical Systems International AG, Cham (CH)

( * ) Notice: Subject to any disclaimer, the term of this patent is extended or adjusted under 35 U.S.C. 154(b) by 0 days.

(21) Appl. No.: 15/391,058

(22) Filed: Dec. 27, 2016

(65) Prior Publication Data

US 2018/0178036 A1  Jun. 28, 2018

(51) Int. Cl.
*A61N 5/10* (2006.01)

(52) U.S. Cl.
CPC ......... *A61N 5/1031* (2013.01); *A61N 5/1077* (2013.01); *A61N 2005/1041* (2013.01)

(58) Field of Classification Search
CPC .... A61N 5/103; A61N 5/1031; A61N 5/1038; A61N 2005/1041; A61N 5/1077
See application file for complete search history.

(56) References Cited

U.S. PATENT DOCUMENTS

| 5,394,452 | A | 2/1995 | Swerdloff et al. |
| 5,724,400 | A | 3/1998 | Swerdloff et al. |
| 8,644,571 | B1 | 2/2014 | Schulte et al. |
| 9,901,749 | B2 | 2/2018 | Van Heteren et al. |
| 2005/0111621 | A1* | 5/2005 | Riker ............. A61N 5/1031 378/65 |
| 2009/0154644 | A1 | 6/2009 | Nord et al. |
| 2009/0326615 | A1 | 12/2009 | Nord et al. |
| 2010/0054410 | A1 | 3/2010 | Nord et al. |
| 2010/0177871 | A1 | 7/2010 | Nord |
| 2010/0232572 | A1 | 9/2010 | Nord et al. |
| 2012/0014507 | A1* | 1/2012 | Wu ................. A61N 5/10 378/65 |
| 2013/0197878 | A1* | 8/2013 | Fiege ............. A61N 5/1031 703/2 |
| 2014/0072109 | A1 | 3/2014 | Van Heteren et al. |
| 2014/0350863 | A1 | 11/2014 | Hartman et al. |
| 2015/0095043 | A1 | 4/2015 | Cordero Marcos et al. |
| 2017/0189715 | A1 | 7/2017 | Isola et al. |
| 2017/0296840 | A1 | 10/2017 | Bokrantz et al. |
| 2017/0340900 | A1 | 11/2017 | Moore et al. |
| 2018/0043182 | A1 | 2/2018 | Wu et al. |

FOREIGN PATENT DOCUMENTS

| CA | 2995473 | 2/2017 |
| CN | 102138155 | 7/2011 |
| CN | 104866928 | 8/2015 |
| CN | 105031819 | 11/2015 |
| CN | 105120955 | 12/2015 |

(Continued)

*Primary Examiner* — Carrie R Dorna

(57) ABSTRACT

A clinical goal for radiation treatment of a patient is set. A dose prediction model is selected from a number of dose prediction models based on the clinical goal. A radiation treatment plan is then generated for the patient using the dose prediction model that was selected based on the clinical goal.

18 Claims, 7 Drawing Sheets

(56) References Cited

FOREIGN PATENT DOCUMENTS

| | | |
|---|---|---|
| EP | 2323732 | 5/2011 |
| WO | WO2014187866 | 11/2014 |
| WO | WO2014139040 | 4/2015 |
| WO | 2015193776 | 12/2015 |
| WO | WO2016001046 | 1/2016 |
| WO | WO2016081916 | 5/2016 |
| WO | WO2016144914 | 9/2016 |

* cited by examiner

SELECTING A DOSE PREDICTION MODEL BASED ON CLINICAL GOALS

RELATED U.S. APPLICATION

This application is related to the U.S. application with Ser. No. 15/403,955, filed Jan. 11, 2017, entitled "Systems and Methods for Generating Radiation Treatment Plans," hereby incorporated by reference in its entirety.

BACKGROUND

The use of radiation therapy to treat cancer is well known. Typically, radiation therapy involves directing a beam of high energy proton, photon, or electron radiation ("therapeutic radiation") into a target volume (e.g., a tumor or lesion).

Before a patient is treated with radiation, a treatment plan specific to that patient is developed. The plan defines various aspects of the therapy using simulations and optimizations based on past experiences. For example, for intensity modulated radiation therapy (IMRT), the plan can specify the appropriate beam type (e.g., flattening filter free type) and the appropriate beam energy. Other parts of the plan can specify, for example, the angle of the beam relative to the patient, the beam shape, the placement of boluses and shields, and the like. In general, the purpose of the treatment plan is to deliver sufficient radiation to the target volume while minimizing exposure of surrounding healthy tissue to the radiation. Treatment plans are usually assessed with the aid of dose-volume histograms (DVHs) that, generally speaking, represent three-dimensional (3D) dose distributions in two dimensions.

In IMRT, the planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one best suited to achieving the desired outcome.

For example, the planner defines a set of quality metrics, such as target homogeneity, critical organ sparing, and the like, and respective target values $Q_i$ for the metrics. For planning, the metrics are defined such that a smaller value is preferred over a larger value. The planner also defines a relative priority or weight $w_i$ for each of the quality metrics. The task of developing an optimal plan is then formulated as a quadratic cost function C: $C=\text{sum}(w_i(Q_i-q_i)^2)$, where $q_i$ is the value of the quality metric that can be achieved for a particular treatment plan. The optimal plan is determined by minimizing the cost function C.

Often it is not easy to determine an optimal plan based solely on the cost function. For instance, the optimal solution of the cost function may not necessarily describe the clinically best balance between quality metrics, or the 3D dose distribution might have some undesirable features that are difficult to represent as a quality metric.

One way to assist the planner is a knowledge-based approach that automatically generates objective functions so that the resulting plan incorporates and reflects present practices utilized in creating the knowledge base. This typically captures the best practices utilized at a treatment center, but can also be based on larger knowledge bases of well-defined treatments gathered from multiple treatment centers. A treatment plan developed in this manner can be referred to as a balanced plan.

Another way to assist the planner is to use a multi-criteria optimization (MCO) approach for treatment planning. Pareto surface navigation is an MCO technique that facilitates exploration of the tradeoffs between clinical goals. For a given set of clinical goals, a treatment plan is considered to be Pareto optimal if it satisfies the goals and none of the metrics can be improved without worsening at least one of the other metrics. The set of Pareto optimal plans, which also may be referred to as anchor plans, define a Pareto surface related to the set of clinical goals. Movement along the Pareto surface results in tradeoffs between the clinical goals; some metrics will improve at the cost of worsening one or more other metrics. The planner can navigate along the Pareto surface and choose a treatment plan that seems to be the best according to the criteria applied by the planner, or a treatment plan can be selected automatically based on its proximity to the Pareto surface.

However, it can be difficult to define a clinically meaningful point in the domain represented by the Pareto surface, and thus the planner might like to search for treatment plans that are outside of that domain. Thus, a technique that increases the versatility of current approaches and makes MCO more effective for a variety of clinical goals would be of value.

Also, as the number of criteria in MCO increases, the challenges faced by the planner while navigating the Pareto surface also increase. Conventionally, navigation is accomplished using sliders in a graphical user interface. A separate, one-dimensional slider is provided for each quality metric. When the planner selects and moves one slider to change the value of the associated quality metric, the other sliders may move in response to reflect changes in the values of their associated quality metrics caused by the change in value of the selected quality metric. When there is a relatively large number of quality metrics (e.g., seven or more), navigation of the Pareto surface can be complicated, and the results of navigating the Pareto surface can be difficult to interpret.

SUMMARY

In an embodiment, a clinical goal or a set of clinical goals for radiation treatment of a patient is set. A dose prediction model is selected from a number of dose prediction models based on the clinical goal or goals. A radiation treatment plan is then generated for the patient using the dose prediction model that was selected based on the clinical goal or goals. In a set of clinical goals, the clinical goals can be weighted equally or differently from one another.

The selected dose prediction model is generated using training data based on a sample of other radiation treatment plans that all have the same clinical goal or the same set of clinical goals. Each of the other dose prediction models is also generated using training data based on a respective sample of radiation treatment plans that have the same respective clinical goal or the same respective set of clinical goals. Each prediction model can thus be indexed by the clinical goal or goals used to train the model. In an embodiment, each clinical goal is in a format that is parsable by an application that is used to select the dose prediction model. Thus, a planner can input the clinical goal(s), and the application can identify the clinical goal(s) and select a dose prediction model accordingly.

In an embodiment, the radiation treatment plan that is generated using the selected dose prediction model is a balanced plan that is generated using radiation treatment plans accessed from a knowledge base. This approach is referred to herein as knowledge-based planning.

In an embodiment, the values of the quality metrics associated with the balanced plan are varied one at a time (e.g., at increments from their smallest to their largest possible values) to generate anchor plans that form or define a Pareto surface.

By including the use of a clinical goal or set of clinical goals to select a dose prediction model for knowledge-based planning, the balanced plan can be more refined because the selected dose prediction model was trained using those clinical goals. By creating treatment plans that consider different clinical goals or different emphasis on (weighting of) the clinical goals, the region around the balanced plan can be expanded to include regions that may not have been previously available for evaluation. Accordingly, embodiments according to the present invention are more versatile and the effectiveness of MCO for a variety of clinical goals is increased.

The Pareto surface can be displayed in a graphical user interface that also includes a number of sliders corresponding to a subset of less than the number of quality metrics associated with the balanced plan and used to generate the anchor plans. The subset is selected according to a criterion such as but not limited to a ranking of the quality metrics, a user input, a correlation between two or more of the quality metrics, and a knee point in the Pareto surface.

Thus, the number of sliders is reduced so that the planner can focus on the most significant quality metrics and tradeoffs. Navigation of the Pareto surface is less complicated and it is easier to interpret the results of navigating the Pareto surface.

This summary is provided to introduce a selection of concepts in a simplified form that is further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Figure 1:
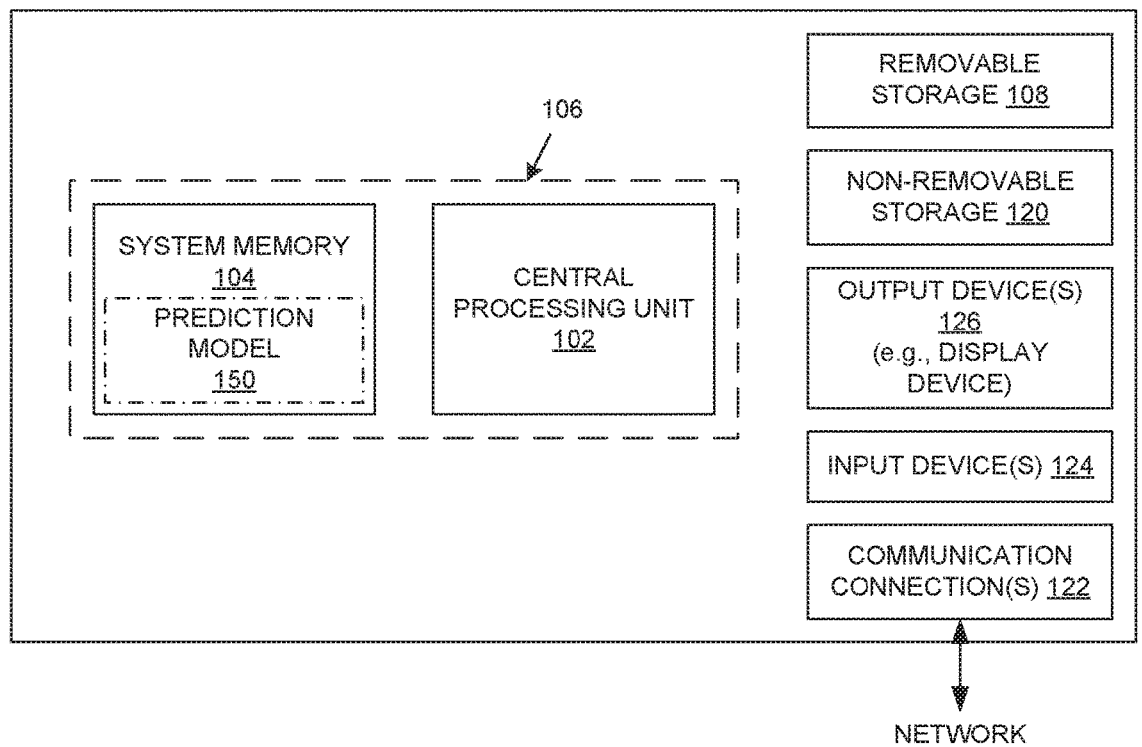
FIG. 1 shows a block diagram of an example of a computing system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "selecting," "using," "inputting," "receiving," "generating," "varying," "parsing," "navigating," "displaying," or the like, refer to actions and processes (e.g., the flowcharts 700 and 800 of FIGS. 7 and 8, respectively) of a computing system or similar electronic computing device or processor (e.g., the computing system 100 of FIG. 1). The computing system or similar electronic computing device manipulates and transforms data represented as physical (electronic) quantities within the computing system memories, registers or other such information storage, transmission or display devices.

Portions of the detailed description that follows are presented and discussed in terms of a method. Although steps and sequencing thereof are disclosed in figures herein (e.g., FIGS. 7 and 8) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computing system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included.

In the example of FIG. 1, the memory 104 includes computer-readable instructions, data structures, program modules, and the like associated with a dose prediction model 150. However, the dose prediction model 150 may instead reside in any one of the computer storage media used by the system 100, or may be distributed over some combination of the computer storage media, or may be distributed over some combination of networked computers.

Figure 2:
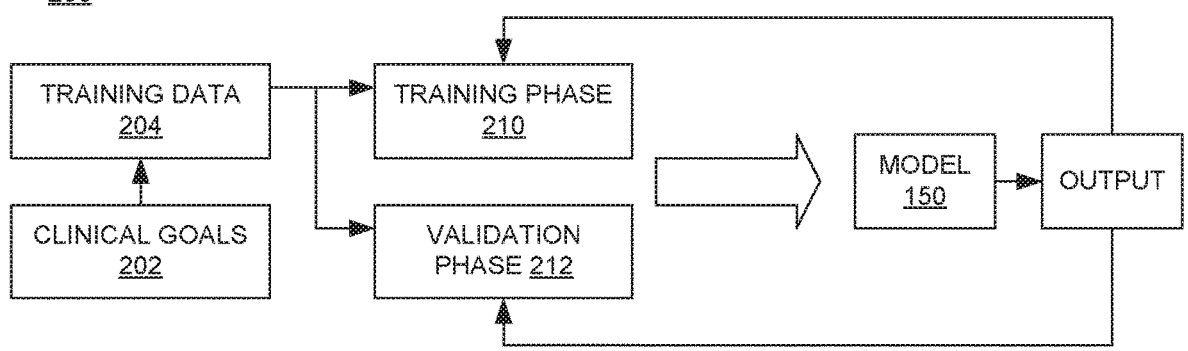
FIG. 2 shows a process that can be implemented to create and use a dose prediction model in an embodiment according to the present invention.

FIG. 2 shows a process 200 that can be implemented to create (train and validate) the dose prediction model 150 in an embodiment according to the present invention. Process 200 can be implemented as computer-readable instructions stored in a computer-usable medium and executed on a computing system like the system 100 of FIG. 1.

The clinical goals 202 of FIG. 2 include (as computer-readable data) a clinical goal or set of clinical goals. In general, a clinical goal is a factor that is related to treatment outcome. The clinical goals offer leeway in the trade-off between the competing objectives of delivering doses to a target volume (e.g., diseased tissue) while minimizing doses to surrounding (e.g., healthy) tissue.

The clinical goals are used to guide the development of a radiation treatment plan describing, among other parameters, the type of radiation to be used, the orientation of the radiation therapy beams to be directed toward patient at multiple beam stations, the shape for collimation of the beams, and the amount of dose to be delivered at each station. A clinical goal may also define constraints or goals for quality metrics such as minimum and maximum dose amounts and mean dose for particular tissue volumes (called regions of interest or ROIs), dose homogeneity, target volume dose distribution, organ-at-risk dose distributions, other normal tissue dose distributions, and other spatial dose distributions. That is, as used herein, a clinical goal is different from but may be related to a quality metric. For example, a clinical goal might be phrased as "achieve the target dose homogeneity limit on the ROI and do not exceed the dose limit on any overlapping organs." In this example, the quality metrics could include numerical values for target dose homogeneity on the ROI and dose limits for each overlapping organs. During development of a final radiation treatment plan, various treatment plans are evaluated by determining a value for these quality metrics and comparing them against their limits and the clinical goals. As will be described, in an embodiment, the treatment plans are evaluated by generating a balanced plan using knowledge-based planning and then generating anchor plans based on the balanced plan.

Continuing with reference to FIG. 2, the training data 204 includes, for example, computer-readable data from previous and existing radiation treatment plans that will be used to generate a dose prediction model. The training data is based on a sample of different treatment plans developed for various patients. The training data may include, for example, dose-volume histograms (DVHs) for the first sample of treatment plans.

Embodiments according to the present invention consider the clinical goals 202 during training and validation of each dose prediction model. Consider an example in which there are two dose prediction models. Each of the prediction models is trained using a respective set of training data. In embodiments according to the invention, the first dose prediction model is generated using training data from previous and existing radiation treatment plans that were/are based on a first clinical goal or a first set of clinical goals, and the second dose prediction model is generated using training data from previous and existing radiation treatment plans that were/are based on a second clinical goal or a second set of clinical goals (different from the first).

The process 200 is now described for a dose prediction model 150 using a first set of training data 204 that considers a first clinical goal or a first set of clinical goals 202 as just described. For ease of discussion, such training data will be referred to herein as goal-specific training data. The process 200 can be repeated for each dose prediction model that is to be generated using the appropriate goal-specific training data as described in the above example.

In the model training phase 210, the dose prediction model 150 is developed and trained using the goal-specific training data 204. In the model validation phase 212, the dose prediction model 150 is evaluated based on its performance on the goal-specific training data (e.g., its ability to accurately model the training data and the DVHs for the training data) as well as its ability to satisfactorily predict validation data based on another (second) sample of treatment plans (e.g., its ability to accurately model the validation data and the DVHs for the validation data). The adequacy of the dose prediction model 150 is demonstrated by its capability to satisfactorily model and predict both the goal-specific training data and the validation data.

Goal-specific training data included in the model training phase 210 can be appropriately considered and assessed using a regression model, for example, until the dose prediction model 150 is produced. Once the goal-specific training data can be satisfactorily predicted using the dose prediction model 150, then the data included in the validation phase 212 can be used to independently test and verify the accuracy of the model. Model development is an iterative process between training and validation that proceeds until the validation data is satisfactorily predicted.

In this manner, a dose prediction model (the model 150) that is based on a particular clinical goal or set of clinical goals is generated. As noted, the process 200 can be repeated using different sets of training data and clinical goal(s) to create additional dose prediction models. Each dose prediction model can be identified by its own unique model identifier (ID). Metadata for a dose prediction model can be stored with the model or associated with the model in a database using the model ID. Model data (e.g., data to be used by the data prediction model 150) can also be stored with the model or associated with the model in a database using the model ID.

The dose prediction model 150 may be used to predict dose parameters for a treatment plan corresponding to a particular patient. The dose prediction model 150 may be implemented as a DVH estimation model, where the predicted quantity is a dose volume histogram. In other embodiments, the prediction model 150 also generates a prediction based on a distance to a target (DTH) histogram, which expresses the distance from an ROI to a radiation target. In yet other embodiments, the dose prediction model 150 is implemented as any other model suitable for predicting dosage (as a dose histogram or spatial 3D dose distribution) for a radiation treatment plan.

The dose prediction model 150 can then be used to develop a radiation treatment plan for a particular patient by receiving patient-specific information (e.g., geometry information) that is input to and processed by the model. The input patient-specific information may contain any combination of parameters that can practically affect the radiation treatment plan. For example, the patient-specific information may be organized as a vector or a data structure including feature elements for: size and shape of the target volume; location of the target volume; size and shape of an organ at risk; type of an organ at risk; a part of the target volume that overlaps an organ; and a part of an organ that overlaps the target volume.

Figure 3:
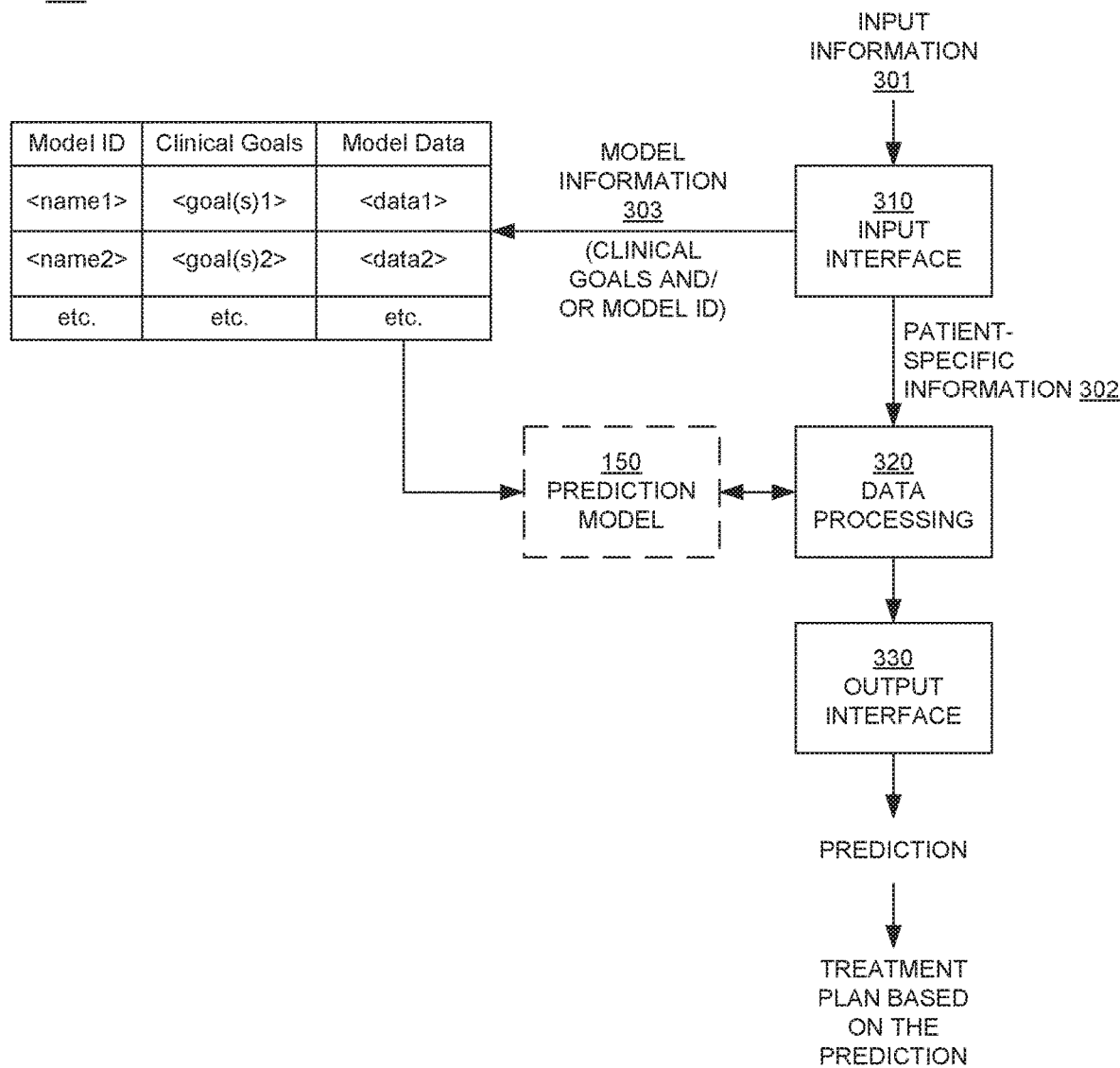
FIG. 3 is a block diagram illustrating an example of an automated radiation treatment planning system in an embodiment according to the present invention.

FIG. 3 is a block diagram illustrating an example of an automated radiation treatment planning system 300 in an embodiment according to the present invention. The system 300 includes an input interface 310 to receive input information 301, a data processing component 320 that implements the dose prediction model 150, and an output interface 330. The system 300 in whole or in part may be implemented as a software program, hardware logic, or a combination thereof on/using the computing system 100 (FIG. 1).

The input information 301 includes the patient-specific information 302 (such as that described above) and also includes model information 303. The model information 303 includes one or more clinical goals. The clinical goal or goals are used by an application executed by the system 300 to automatically select an appropriate dose prediction model 150. That is, the dose prediction model 150 is selected according to the clinical goal(s) that are input to the system 300. Alternatively, a lookup can be performed based on the input clinical goal(s), and a model ID corresponding to the goal(s) can be identified and used to select the appropriate dose prediction model 150. In an embodiment, each clinical goal is in a format that is parsable by the application that is used to select the dose prediction model.

The patient-specific information 302 is provided to and processed by the dose prediction model 150. The dose prediction model 150 yields a prediction result, e.g., an achievable dose distribution prediction. A radiation treatment plan based on the prediction result can then be generated. In an embodiment, the prediction result is accompanied by parameters indicative of the quality of the prediction, such as reliability of the result (e.g., affected by the internal coherence of the training data), complexity of the predicted plan, and probability of the result.

Figure 4:
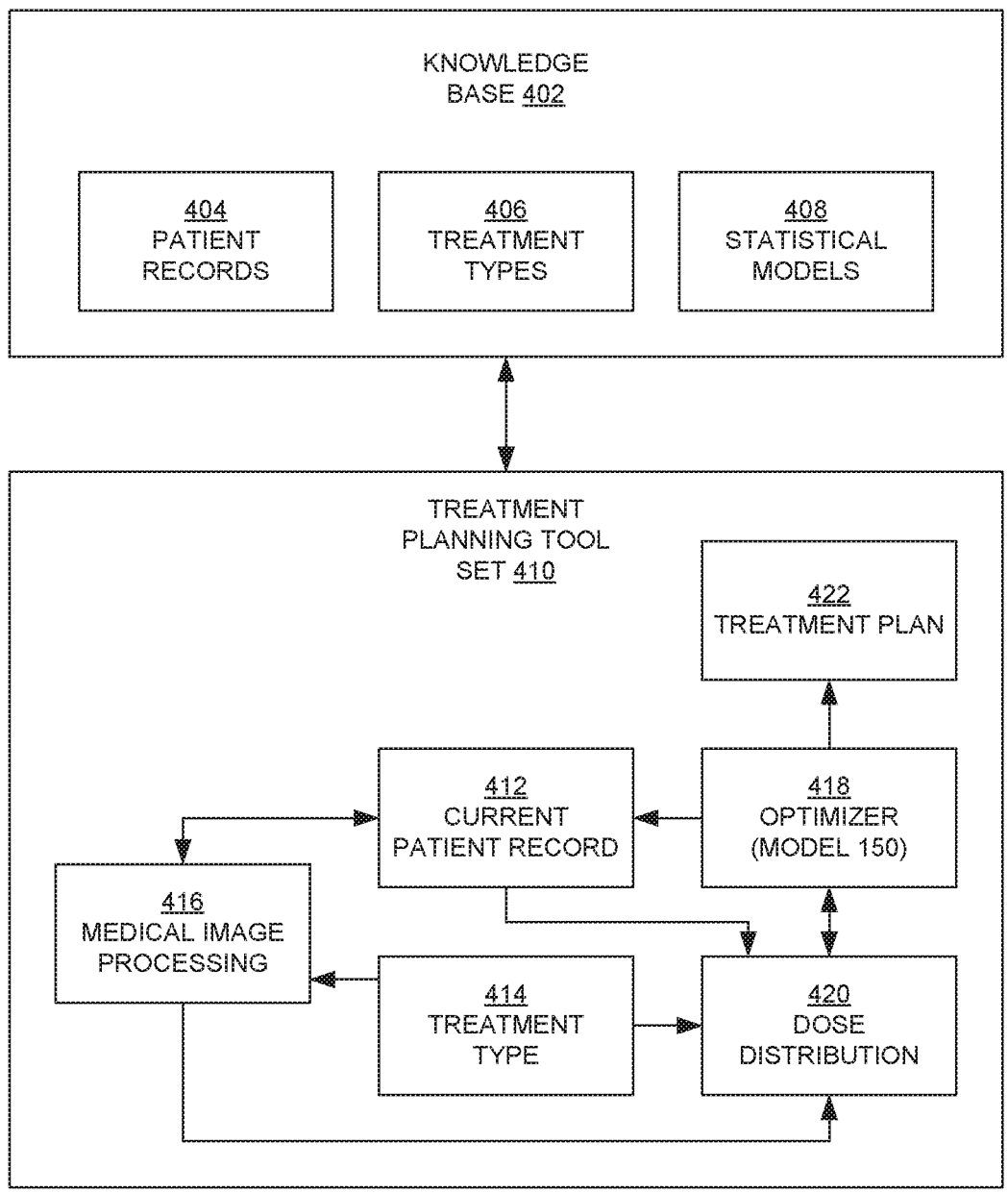
FIG. 4 illustrates an embodiment of a knowledge-based planning system in an embodiment according to the present invention.

FIG. 4 illustrates an embodiment of a knowledge-based planning system 400 incorporating a combination of patient records and statistical models for generating radiation treatment plans in an embodiment according to the present invention. In the example of FIG. 4, the system 400 includes a knowledge base 402 and a treatment planning tool set 410. The knowledge base 402 includes patient records 404 (e.g., radiation treatment plans), treatment types 406, and statistical models 408. The treatment planning tool set 410 in the example of FIG. 4 includes a current patient record 412, a treatment type 414, a medical image processing module 416, an optimizer 418, a dose distribution module 420, and a final radiation treatment plan 422.

The treatment planning tool set 410 searches through the knowledge base 402 (through the patient records 404) for prior patient records that are similar to the current patient record 412. The statistical models 408 can be used to compare the predicted results for the current patient record 412 to a statistical patient. Using the current patient record 412, a selected treatment type 406, and selected statistical models 408, the tool set 410 generates a radiation treatment plan 422. A radiation treatment plan developed in this manner (e.g., the treatment plan 422) can be referred to as a balanced plan.

More specifically, based on past clinical experience, when a patient presents with a particular diagnosis, stage, age, weight, sex, co-morbidities, etc., there can be a treatment type that is used most often. By selecting the treatment type that the planner has used in the past for similar patients, a first-step treatment type 414 can be chosen. The medical image processing module 416 provides automatic contouring and automatic segmentation of two-dimensional cross-sectional slides (e.g., from computed tomography or magnetic resonance imaging) to form a 3D image using the medical images in the current patient record 412. Dose distribution maps are calculated by the dose distribution module 420.

The knowledge base 402 can be searched for a combination of objectives that can be applied by the optimizer 418 to determine a dose distribution. For example, an average organ-at-risk dose-volume histogram, a mean cohort organ-at-risk dose-volume histogram, and average organ-at-risk objectives can be selected from the knowledge base 402. In embodiments according to the present invention, the optimizer 418 uses the dose prediction model 150 to help shape the dose distribution. Accordingly, the optimizer 418 can provide a 3D dose distribution, fluences, and associated dose-volume histograms for the current patient. By using the dose prediction model 150, which is trained and validated as described above, those results are expected to fall within the historically accepted range for a patient with a similar disease type and treatment type.

In an embodiment, the values of the quality metrics associated with the balanced plan (the treatment plan 422) are varied one at a time (e.g., at increments from their smallest to their largest possible values) to generate anchor plans (Pareto optimal plans) that form or define a Pareto surface that can be used in a multi-criteria optimization (MCO) approach for radiation treatment planning.

In another embodiment, the clinical goals can be varied (that is, different dose prediction models can be selected based on a different clinical goal or goals) and other balanced plans can be generated. The other balanced plans can be represented graphically (e.g., as a Pareto surface) and/or can be used to generate additional anchor plans that can be represented as a Pareto surface. By browsing through the other balanced plans, the planner can visualize the tradeoffs made in the various plans.

Figure 5:
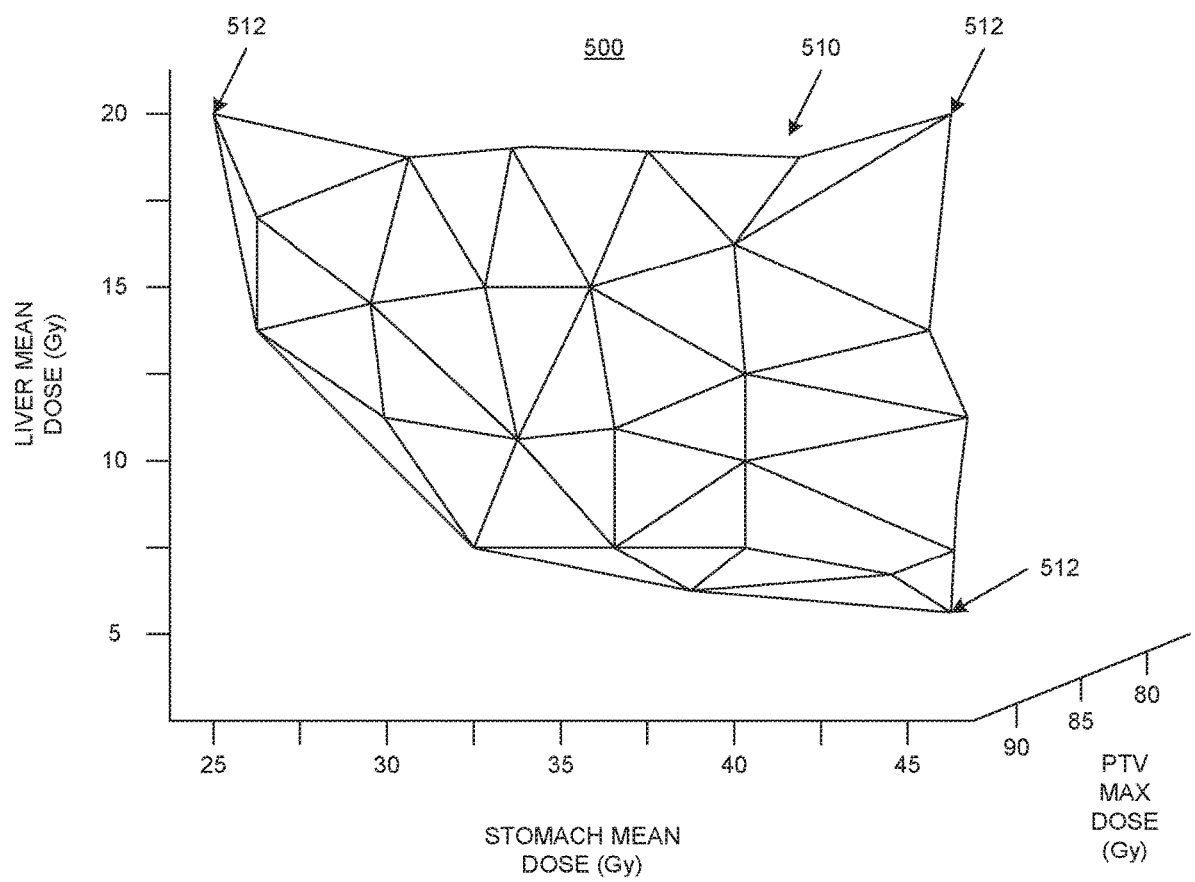
FIG. 5 illustrates an example of a first element of a graphical user interface in an embodiment according to the present invention.

FIG. 5 illustrates an example of a first element of a graphical user interface (GUI) 500 that can be displayed on an output device 126 (a display device) of the computing system 100 (FIG. 1) in an embodiment according to the present invention. In the example of FIG. 5, the first element includes a representation of a Pareto surface 510. As noted above, the Pareto surface 510 represents a set of anchor plans 512 that are generated using a balanced plan that is generated using a dose prediction model 150 that is selected according to a clinical goal or set of clinical goals and was trained and validated using that goal or those goals as previously described herein (not all of the anchor plans are indicated in the figure). In essence, the anchor plans represent the best point in each dimension of the Pareto surface 510. The balanced plan (not represented in the figure) may lie on the Pareto surface 510 or it may lie within the hull of the convex surface.

Figure 6:
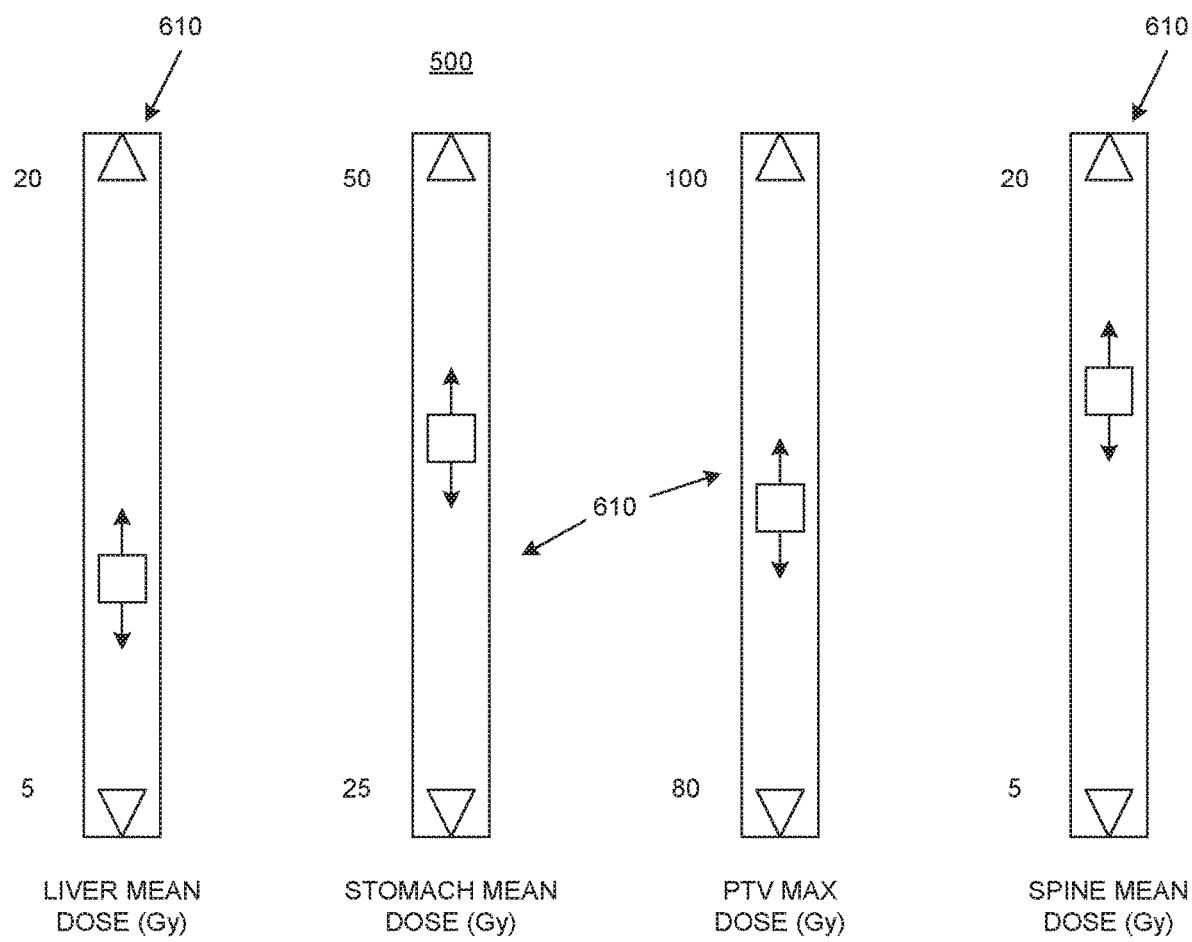
FIG. 6 illustrates an example of a second element of a graphical user interface in an embodiment according to the present invention.

FIG. 6 illustrates an example of a second element of the GUI 500 that can be displayed on an output device 126 (a display device) of the computing system 100 (FIG. 1) in an embodiment according to the present invention. In the example of FIG. 6, the second element includes a number of interactive sliders 610. The sliders 610 can be used to navigate the Pareto surface 510 of FIG. 5. Each of the sliders 610 corresponds to a respective quality metric. In an embodiment, the quality metrics are specified such that a smaller value is better, in which case the sliders 610 in the example of FIG. 6 are configured so that moving a slider down results in an improvement in the corresponding quality metric. Movement of one or more of the sliders 610 may change the positions of one or more of the other sliders. Different types of sliders, oriented the same or differently from the sliders 610, can be used; that is, the invention is not limited to the type or orientation of the sliders in the example of FIG. 6.

Significantly, the number of sliders 610 included in the GUI 500 is less than the number of quality metrics associated with the balanced plan and used to generate the anchor plans. In general, the subset of the quality metrics represented by the sliders 610 is selected according to a criterion such as but not limited to a ranking of the quality metrics, a user input, a correlation between two or more of the quality metrics, and a knee point in the Pareto surface. While three sliders are shown in FIG. 6, the present invention is not so limited. That is, in particular, the number of sliders is not limited to the number of dimensions shown in the first GUI element, nor do the sliders need to correspond to the names on the axes of the Pareto surface 510. For example, as shown in the example of FIG. 6, there can be a fourth slider associated with spinal dose even though the Pareto surface in the example of FIG. 5 does not have an axis labeled as such. Movement of the fourth slider may change the positions of the other three sliders and hence can still affect the navigation of the Pareto surface.

The user input may include a selection of the quality metrics to be represented in the GUI 500. For example, a planner can be presented with a list of all quality metrics associated with the Pareto surface 510 and can select which quality metrics are to be represented using one of the sliders 610. Different quality metrics are related to clinical goals with different priorities. The priorities can be specified by the planner before MCO is executed or they can be defined in a template or protocol. One criterion that can be used is to select quality metrics that are related to higher priority clinical goals. It is possible that the quality metrics are related to multiple clinical goals with varying priorities. In that case, the selection criterion can be weighted by the clinical goal that can be achieved using the set of treatment plans used in MCO (e.g., within the ranges that can be navigated on the Pareto surface 510).

Another criterion that can be used for selecting which quality metrics are to be represented using the sliders 610 is based on an analysis of the correlation between quality metrics. Different quality metrics may be highly correlated to one another. When there are strongly correlated quality metrics, the quality metric whose value drives the values of the other, correlated quality metrics can be selected and the other correlated quality metrics may not be selected.

Even if quality metrics are not highly correlated, the Pareto surface between them may have a significant knee point (a point at which a small change in the value of one of the quality metrics causes a large change in the value of another one of the quality metrics). In such cases, it is unlikely that the planner will need to tune the mutual balance of these quality metrics and can select one but not the other.

It is also possible to combine and represent multiple quality metrics using a single slider. Also, even if a quality metric is not selected, its value can still be calculated when the sliders are moved and can be presented in the GUI 500 (e.g., in a table).

The selection of which quality metrics to represent using the sliders 610 can be done by the planner or it can be done automatically based on the above criteria. If done automatically, the planner can make adjustments to the number of sliders 610 and to the quality metrics selected.

Figure 7:
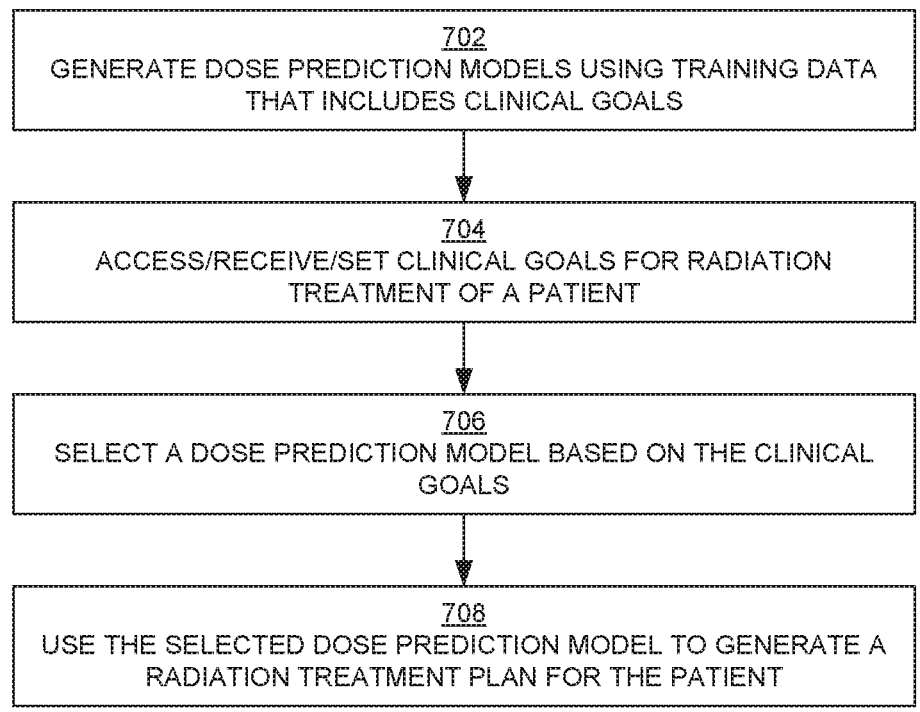
FIG. 7 is a flowchart of an example of a computer-implemented method for generating a radiation treatment plan in an embodiment according to the present invention.

FIG. 7 is a flowchart 700 of an example of a computer-implemented method for generating a radiation treatment plan in an embodiment according to the present invention. The flowchart 700 can be implemented as computer-executable instructions residing on some form of computer-readable storage medium (e.g., using the computing system 100 of FIG. 1).

In block 702 of FIG. 7, dose prediction models are generated using respective sets of training data, where each of the sets of training data based on a respective clinical goal or set of clinical goals. In an embodiment, the dose prediction models are generated as described above in conjunction with FIG. 2, for example.

In block 704 of FIG. 7, a clinical goal or a set of clinical goals for radiation treatment of a patient is set, accessed, or received.

In block 706, a dose prediction model is selected from the dose prediction models (block 702) based on the clinical goal or goals (block 704).

In block 708, a radiation treatment plan is generated for the patient using the dose prediction model (block 706) that was selected based on the clinical goal or goals as described above in conjunction with FIG. 3, for example.

In an embodiment, the radiation treatment plan that is generated using the selected dose prediction model is a balanced plan that is generated using radiation treatment plans accessed from a knowledge base as described in conjunction with FIG. 4, for example. In an embodiment, the values of the quality metrics associated with the balanced plan are varied one at a time (e.g., at increments from their smallest to their largest possible values) to generate anchor plans that form or define a Pareto surface.

By including the use of a clinical goal or set of clinical goals to select a dose prediction model for knowledge-based planning, the balanced plan can be more refined because the selected dose prediction model was trained using those clinical goals. By creating treatment plans that consider different clinical goals or different emphasis on (weighting of) the clinical goals, the region around the balanced plan can be expanded to include regions that may not have been previously available for evaluation. Accordingly, embodiments according to the present invention are more versatile and the effectiveness of MCO for a variety of clinical goals is increased.

The Pareto surface can be displayed in a graphical user interface that also includes a number of sliders corresponding to a subset of less than the number of quality metrics associated with the balanced plan and used to generate the anchor plans. The subset is selected according to a criterion such as but not limited to a ranking of the quality metrics, a user input, a correlation between two or more of the quality metrics, and a knee point in the Pareto surface.

Figure 8:
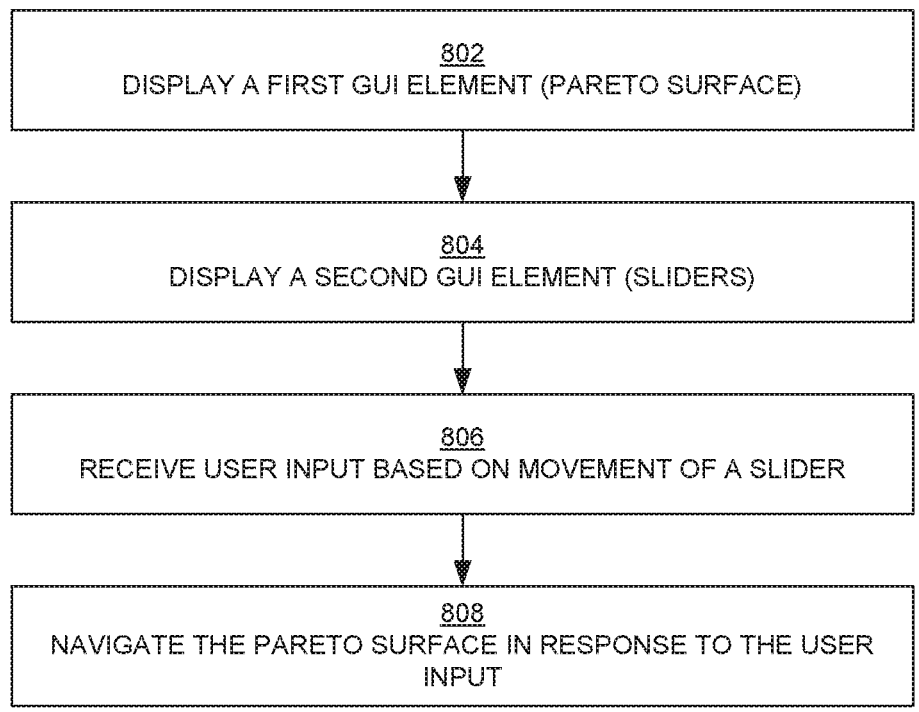
FIG. 8 is a flowchart of an example of a computer-implemented method for generating a radiation treatment plan in an embodiment according to the present invention.

FIG. 8 is a flowchart 800 of an example of a computer-implemented method for generating a radiation treatment plan in an embodiment according to the present invention. The flowchart 800 can be implemented as computer-executable instructions residing on some form of computer-readable storage medium (e.g., using the computing system 100 of FIG. 1).

In block 802 of FIG. 8, a first element of a GUI is displayed on a display device of the computing system 100 (FIG. 1). In an embodiment, the first element includes a Pareto surface representing a number of radiation treatment plans (e.g., anchor plans) as described above in conjunction with FIG. 5, for example.

As described herein, there are a number of quality metrics and respective quality metric values associated with the radiation treatment plans that are represented in the display. In an embodiment, the radiation treatment plans are generated by varying the quality metric values one at a time in a dose prediction model that is selected according to a clinical goal specified for the radiation treatment plans as described herein.

In block 804 of FIG. 8, a second element of the GUI is also displayed on the display device. In an embodiment, the second element includes a number of sliders corresponding to a subset of less than the number of quality metrics (the number of sliders is less than the number of quality metrics considered in the development of the balanced and anchor plans) as described above in conjunction with FIG. 6, for example. Thus, the number of sliders is reduced so that the planner can focus on the most significant quality metrics and tradeoffs. Navigation of the Pareto surface is less complicated and it is easier to interpret the results of navigating the Pareto surface.

In block 806 of FIG. 8, a user input based on a movement of at least one of the sliders is received.

In block 808, the Pareto surface (block 802) is navigated in response to the user input.

Embodiments according to the invention are thus described. These embodiments can be used to plan different types of external beam radiotherapy other than IMRT including, for example, image-guided radiotherapy (IGRT), RAPIDARC™ radiotherapy, stereotactic body radiotherapy (SBRT), and stereotactic ablative radiotherapy (SABR).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer-implemented method, comprising:
   accessing a clinical goal for radiation treatment of a patient, wherein the clinical goal defines a constraint for a quality metric associated with the radiation treatment of the patient, wherein the quality metric comprises a predicted numerical value for a result generated according to the radiation treatment plan;
   selecting a first dose prediction model from a plurality of dose prediction models according to the clinical goal; and
   generating a radiation treatment plan for the patient, said generating comprising executing the first dose prediction model selected according to the clinical goal.

2. The method of claim 1, wherein the first dose prediction model is generated using training data based on a sample of other radiation treatment plans that also have the clinical goal.

3. The method of claim 1, wherein each dose prediction model of the plurality of dose prediction models is indexed by a respective clinical goal and wherein said each dose prediction model is generated using training data based on a respective sample of radiation treatment plans that have the same respective clinical goal.

4. The method of claim 1, wherein said generating further comprises:
   accessing radiation treatment plans in a knowledge base; and
   using the radiation treatment plans to generate the radiation treatment plan.

5. The method of claim 1, wherein said generating further comprises:
   accessing radiation treatment plans in a knowledge base;
   using the radiation treatment plans to generate a balanced plan, wherein the balanced plan has associated therewith a number of quality metrics and respective quality metric values; and
   varying the quality metric values one at a time to generate anchor plans that define a Pareto surface.

6. The method of claim 5, further comprising navigating the Pareto surface in a graphical user interface that also comprises a number of sliders corresponding to a subset of less than the number of quality metrics.

7. The method of claim 6, wherein the subset is selected according to a criterion selected from the group consisting of: a ranking of the quality metrics; a user input; a correlation between two or more of the quality metrics; and a knee point in the Pareto surface.

8. The method of claim 1, wherein the clinical goal is in a format that is parsable by an application that performs said selecting.

9. A computing system comprising:
a central processing unit (CPU); and
memory coupled to the CPU and having stored therein instructions that, if executed by the computing system, cause the computing system to execute operations comprising:
  accessing a knowledge base comprising a listing of a plurality of dose prediction models, wherein each dose prediction model of the plurality of dose prediction models is indexed by a respective clinical goal;
  accessing a clinical goal for radiation treatment of a patient;
  selecting a first dose prediction model from the plurality of dose prediction models, wherein the first dose prediction model is indexed by the clinical goal for the radiation treatment of the patient, wherein the clinical goal defines constraints for quality metrics for the radiation treatment of the patient and is in a format that is parsable by an application that performs said selecting; and
  generating a radiation treatment plan for the patient, said generating comprising executing the first dose prediction model selected according to the clinical goal.

10. The system of claim 9, wherein said each dose prediction model is generated using training data based on a respective sample of radiation treatment plans that have the same respective clinical goal.

11. The system of claim 9, wherein the radiation treatment plan is a balanced plan, wherein said generating further comprises:
  accessing radiation treatment plans in the knowledge base; and
  using the radiation treatment plans to generate the balanced plan.

12. The system of claim 9, wherein said generating further comprises:
  accessing radiation treatment plans in the knowledge base;
  using the radiation treatment plans to generate a balanced plan, wherein the balanced plan has associated therewith a number of the quality metrics and respective quality metric values; and
  varying the quality metric values one at a time to generate anchor plans that define a Pareto surface.

13. The system of claim 12, further comprising an output device operable for displaying a graphical user interface comprising the Pareto surface and a number of sliders corresponding to a subset of less than the number of the quality metrics, wherein the operations further comprise navigating the Pareto surface in the graphical user interface responsive to movement of the sliders.

14. The system of claim 13, wherein the subset is selected according to a criterion selected from the group consisting of: a ranking of the quality metrics; a user input; a correlation between two or more of the quality metrics; and a knee point in the Pareto surface.

15. A computing system, comprising:
a central processing unit (CPU);
an output device comprising a display device coupled to the CPU;
memory coupled to the CPU and having stored therein instructions that, when executed by the computing system, cause the computing system to execute a method comprising:
  accessing a knowledge base comprising a listing of a plurality of dose prediction models, wherein each dose prediction model of the plurality of dose prediction models is indexed by a respective clinical goal;
  selecting a dose prediction model from the plurality of dose prediction models according to a clinical goal specified for a plurality of radiation treatment plans, wherein the clinical goal defines constraints for quality metrics for radiation treatment of a patient and is in a format that is parsable by an application that performs said selecting, and wherein the dose prediction model is indexed by the clinical goal specified for the plurality of radiation treatment plans;
  displaying, on the display device, a first element of a graphical user interface, the first element comprising a Pareto surface representing the plurality of radiation treatment plans, wherein there are a number of the quality metrics and respective quality metric values associated with the radiation treatment plans and wherein the radiation treatment plans are generated by varying the quality metric values one at a time in the dose prediction model; and
  displaying, on the display device, a second element of the graphical user interface, the second element comprising a number of sliders corresponding to a subset of less than the number of the quality metrics.

16. The system of claim 15, wherein the method further comprises:
  receiving an input indicating movement of at least one of the sliders; and
  navigating the Pareto surface in the graphical user interface responsive to the input.

17. The system of claim 15, wherein the subset is selected according to a criterion selected from the group consisting of: a ranking of the quality metrics; a user input; a correlation between two or more of the quality metrics; and a knee point in the Pareto surface.

18. The system of claim 15, wherein the dose prediction model is generated using training data based on other radiation treatment plans that also have the clinical goal.

* * * * *